United States Patent [19]

King

[11] Patent Number: 4,814,537
[45] Date of Patent: * Mar. 21, 1989

[54] OXIDATIVE COUPLING OF METHYL-SUBSTITUTED BENZENES

[75] Inventor: Stanley S. T. King, Midland, Mich.

[73] Assignee: The Dow Chemical Company, Midland, Mich.

[*] Notice: The portion of the term of this patent subsequent to Feb. 23, 2005 has been disclaimed.

[21] Appl. No.: 108,187

[22] Filed: Oct. 14, 1987

Related U.S. Application Data

[63] Continuation-in-part of Ser. No. 906,472, Sep. 12, 1986, Pat. No. 4,727,208.

[51] Int. Cl.$^4$ ................................. C07C 2/72
[52] U.S. Cl. ..................... 585/428; 585/426
[58] Field of Search ................. 585/426, 428

[56] References Cited

U.S. PATENT DOCUMENTS

| 2,904,580 | 9/1959 | Idol, Jr. | 260/465.3 |
| 4,151,213 | 4/1979 | Fields | 585/443 |
| 4,390,728 | 6/1983 | Daniel | 568/431 |

FOREIGN PATENT DOCUMENTS

| 0148544 | 7/1985 | European Pat. Off. |
| 24323 | 2/1982 | Japan . |
| 121238 | 7/1983 | Japan . |

OTHER PUBLICATIONS

Chem. Abs., 97(15):126,725m, abstracting Madhock et al., Indian J. Technol., 20(5), 184–89, (1982).
Andersson, J. Catal., 98, 138, (1986).

Primary Examiner—Curtis R. Davis

[57] ABSTRACT

A (methyl-substituted)diphenyl methane such as methyldiphenylmethane is prepared by a coupling reaction wherein a methyl-substituted benzene such as toluene is contacted with a solid heterogeneous catalyst having labile oxygen such as an oxide of vanadium, rhenium or molybdenum. By-product formation, especially the formation of carbon dioxide, is significantly reduced by the practice of this process.

14 Claims, No Drawings

OXIDATIVE COUPLING OF METHYL-SUBSTITUTED BENZENES

CROSS-REFERENCE TO RELATED APPLICATION

This application is a continuation-in-part of application Ser. No. 906,472, filed Sept. 12, 1986, now U.S. Pat. No. 4,727,208.

BACKGROUND OF THE INVENTION

This invention relates to a process for preparing coupled aromatic compounds.

Coupled aromatic compounds such as diphenyl methane and methyl-substituted diphenyl methanes are useful as intermediates for the preparation of anthraquinones which are generally useful as dye intermediates and pulping catalysts.

Anthraquinone has been allegedly prepared by the use of diluted toluene in air (1.2 percent). See, for example, Japan Kokai Nos. 1982-24323 and 1983-121238. Such known processes to prepare anthraquinone by direct toluene oxidation can be generally inefficient. Loss of valuable reactant materials through complete combustion to carbon dioxide can be particularly problematical.

In view of the problems with prior art processes for producing anthraquinones and their precursors, it would be highly desirable to provide a new process for preparing anthraquinones and/or their precursors in high yield.

SUMMARY OF THE INVENTION

The present invention is a process for preparing a (methyl-substituted)diphenyl methane by a coupling reaction which process comprises contacting a methyl-substituted benzene with a solid heterogeneous catalyst having labile oxygen under conditions sufficient to form the (methyl-substituted)diphenyl methane. The catalyst is an oxygen-containing compound of one of the following metals: vanadium, molybdenum, rhenium and tungsten.

The present process is highly efficient in that by-product formation and loss of reactants such as by carbon dioxide formation are greatly minimized. The process can be carried out in either vapor or liquid phases.

The (methyl-substituted)diphenyl methanes produced by the process of this invention are useful as intermediates for preparing anthraquinones which are useful as pulping catalysts and for making dyes.

ILLUSTRATIVE EMBODIMENTS

In general, the methyl-substituted benzenes include compounds represented by the formula

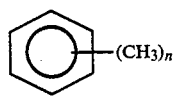
(I)

wherein n is an integer from 1 to 6, preferably from 1 to 5, more preferably from 1 to 3, most preferably 1 or 2. Especially preferred of the methyl-substituted benzenes are toluene and/or xylene. At least one of the methyl-substituted benzenes to be coupled into the methyl-substituted diphenyl methanes must have at least one hydrogen available on the benzene ring.

Benzene itself can be employed as reactant for coupling by the process of the invention, so long as the methyl-substituted benzene is also present as reactant. Hence, "at least" may modify methyl-substituted-diphenyl methane is, to a larger extent, a mixture of coupled products, one of which is diphenyl methane.

In general, the (methyl-substituted)diphenyl methanes are coupled compounds represented by the formula

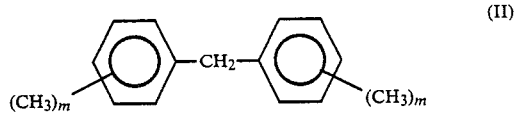
(II)

wherein m is separately at each occurrence an integer from zero to 5 provided that at least one m is one or more, preferably m is zero to 4, most preferably from zero to 2. Especially preferred are those coupled compounds wherein one m value is zero to 2 while the other m value is one. Preferably, at least one methyl group(s) of the compounds of the formula (II) is (are) in a position ortho to the coupled methylene group such as found in o-methyldiphenylmethane, i.e.,

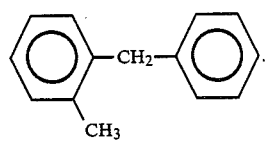

The catalyst employed in the process of the invention is a heterogeneous solid. The solid heterogeneous catalyst contains labile oxygen and is therefore believed to be a reactant-catalyst. The term "reactant-catalyst" means a substance which generally can be considered both or either a reactant and/or a catalyst. As a reactant, the heterogeneous substance generally supplies the labile oxygen to the remaining components of the reaction medium, itself thus losing the oxygen. As a catalyst, the heterogeneous substance generally can be regenerated in the catalytic cycle. The term "labile", which modifies oxygen, means able to be supplied to the remaining components of the reaction medium from the heterogeneous reactant catalyst. As stated hereinbefore, the catalyst is an oxygen-containing compound of a metal such as vanadium, molybdenum, rhenium, and tungsten. Illustratively, the catalyst is represented by the following formula $$M^1_a M^2_b M^3_c O_x \qquad (III)$$

wherein
- $M^1$ is hydrogen;
- $M^2$ is another element from Groups 1a–5a, 1b–7b and 8 of the Periodic Table of Elements as set forth in the *Handbook of Chemistry and Physics*, CRC, 48th Edition (1967–68);
- $M^3$ is at least one of V, Mo, Re or W;
- a is 0 to 10;
- b is 0 to 100;
- c is 0.01 to 100; and
- x is a number which satisfies the average valances of $M^1$, $M^2$ and $M^3$ in the oxidation states in which they exists in reactant-catalyst.

More preferred are the oxides of vanadium, rhenium and molybdenum. Most preferred catalysts are $MoO_3$, $Re_2O_7$ and $V_2O_5$. The catalyst of the invention may be supported with a support such as, for example, silica, titania, alumina, carbon and the like.

For example, toluene reacts with oxygen in metal oxides such as $V_2O_5$, $MoO_3$, bismuthmolybdate-containing catalysts, phosphorus molybdate-containing catalysts and heteropolyoxometalates wherein the metal is V, Mo, Re or W, for example, heteropoly(cage)-molybdates, vanadates and/or tungstates in the absence of gas phase oxygen to form o-methyldiphenylmethane at 150° C. to 500° C. Thus, substances such as these are solid heterogeneous reactant-catalysts having labile oxygen under these conditions. Preferably, the bismuth-molybdate-containing catalyst is such as disclosed in U.S. Pat. No. 2,904,580 (1957) (incorporated herein by reference), which is termed "Type SA" (i.e., Sohio Type A) or more generically termed, a bismuth phosphomolybdate catalyst.

In general, the temperatures of the process are elevated. Elevated temperatures include those such as from 50° C. to 700° C. Preferred elevated temperatures generally range from 100° C. to 500° C. More preferable elevated temperatures for the vapor phase process are generally from 300° C. to about 450° C. Elevated temperatures of the process carried out in the liquid phase may be generally lower than those of the process carried out in the vapor phase. Preferred elevated temperatures can vary with the specific solid heterogeneous reactant-catalyst employed such as illustrated for the vapor phase process by the most preferred temperatures of the following table.

| Catalyst | General Temperature |
| --- | --- |
| Generally, $V_2O_5$ | 350° C. |
| Generally, $MoO_3$ or Type SA | 400° C. |

In general, the liquid phase process is carried out neat, and the vapor phase process can be carried out neat or with an inert gaseous diluent present as a so-called carrier gas. Preferred carrier gases include nitrogen, helium and argon. Unreacted methyl-substituted benzenes are preferred recycled as reactants.

To coupled the methyl-substituted benzenes into the (methyl-substituted)diphenyl methanes, the methyl-substituted benzenes are contacted with the solid heterogeneous catalyst. Oxygen, such as gaseous oxygen, is preferably absence during the coupling. The (methyl-substituted)diphenyl methanes are prepared, and the available labile oxygen of the solid heterogeneous catalyst depletes.

Generally, subsequent to the depletion of the labile oxygen of the solid heterogeneous catalyst, the catalyst is regenerated by contact with oxygen to provide available labile oxygen to the solid heterogeneous catalyst. The regenerative contact is generally with oxygen, for example, gaseous oxygen, including gaseous oxygen dissolved in at least one carrier gas, for example, as in air. The regenerative contact with the oxygen need not be direct as in air contacting the same general site of the prior contact of at least the methyl-substituted benzenes with the now depleted solid heterogeneous catalyst itself, but can be by a more circuitous route such as by diffusion through a solid such as by air contacting the "back side" of the solid heterogeneous catalyst or membrane upon which it can be supported, which is not the same general site as of the prior, or even ongoing, contact of the methyl-substituted benzene(s) with the solid heterogeneous catalyst.

Preferably, the replenishing of the labile oxygen is by air. Multiple alternating beds of solid heterogeneous catalyst at various stages of coupling and depletion of labile oxygen and its regeneration can be employed.

The (methyl-substituted)diphenyl methanes can be recovered, and/or purified if desired, by known procedures. preferred are low temperature vapor traps.

Conversion herein is the molar percent of the organic reactant(s) which is (are) changed into any and all product(s). The conversion can vary widely depending on operating conditions, and can typically be from about one to 80 mole percent. Selectivity herein is the molar percent of a specific product(s) which is (are) prepared, based upon moles of the organic reactant(s) which is (are) converted, that is, based upon the conversion. For example, if 10 moles of the organic reactant toluene are employed and 5 moles of the toluene are changed into any and all product(s), then the conversion is 50 percent. If, of the 5 moles of the toluene which are converted, one mole of the toluene appears as 7 moles of carbon dioxide, then selectivity to carbon dioxide is 20 percent. If, of the 5 moles of the toluene which are converted, 3 moles of the toluene appears as 1.5 moles of a methyldiphenylmethane, then selectivity to methyldiphenylmethane(s) is 60 percent. Preferably, selectivity to the (methyl-substituted)diphenyl methane is at least 20 percent, more preferably at least 40 percent and most preferably at least 60 percent. Concurrently thus, by-product formation can be correspondingly low. Especially notable is the extremely low level of formation of the by-product carbon dioxide which is preferably formed at the selectivity of less than about 65 percent, more preferably less than 30 percent and most preferably less than 10 percent.

SPECIFIC EMBODIMENTS

The following examples further illustrate the invention. Parts, percentages and ratios are by weight unless otherwise specified.

In the following Examples 1-2, the catalyst is packed in a reactor and heated to the desired temperature. The methyl-substituted benzene is fed to the reactor by an inert carrier gas. The products and the unreacted methyl-substituted benzenes are collected at the exit of the reactor. The reactor bed is then purged and regenerated by passing the oxygen containing gas (e.g. air) through the reactor.

EXAMPLE 1 Vapor Phase $MoO_3$ powder (0.109 g) is heated in a quartz tube at 400° C. with helium purge at a constant rate of 30 cc/min. Toluene is introduced into the reactor in the helium stream at a rate of 50 $\mu l$/min. The reaction products are analyzed by an on-line gas chromatograph and an infrared spectrometer, and 70 percent of the product is three methyldiphenylmethane (MDPM) isomers. The other 30 percent contains benzaldehyde, methylbenzophenones, anthraquinone and a small amount of carbon dioxide. The catalyst deactivates the 5 minutes due to the depletion of the oxygen. Methyldiphenylmethane isomers (0.47 mg) are obtained. Upon purging of the toluene from the reactor, air is used to regenerate the catalyst. A total of 55 micromoles of carbon dioxide is collected from the combustion of coke on catalyst. The toluene selectivities to methyldiphenylmethane, coke and others such as benzaldehyde, benzoic acid and benzophenone are 34 percent, 52 percent and 14 percent, respectively.

EXAMPLE 2 Vapor Phase

Trimethyldiphenylmethane (a mixture of at least two isomers) is prepared by following the procedure of Example 1 except that ortho-xylene is employed as the organic reactant. Analysis of the product by gas chromatography shows production of the desired trimethyldiphenylmethane,

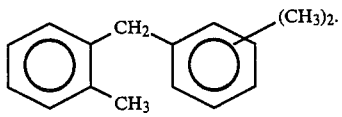

EXAMPLE 3 Liquid Phase

A sample of 0.57 g of toluene is heated with 0.52 g of $V_2O_5$ at 200° C. in a small stainless steel container for 1 hours. One percent of the toluene is converted into methyldiphenylmethane, anthraquinone, benzaldehyde and carbon dioxide at respective selectivities of 70.3 percent, 18.7 percent, 8.2 percent and 2.8 percent.

In the following Examples 4–18, the methyl-substituted benzenes and the reactant catalyst are mixed in a sealed pressure reactor. The reactor is heated to the desired temperature for the desired time. AFter the reaction, the products and the unreacted methyl-substituted benzenes are separated from the solid. The desired products are purified from the mixture. The spent reactant-catalyst is regenerated by heating with oxygen containing gas (e.g. air). The temperature range used is 50° to 700° C. and the heating time used from 1 minute to 24 hours.

EXAMPLE 4

Toluene (0.43 g) and $V_2O_5$ (0.31 g) are heated in a two cc stainless steel reactor to 300° C. for 3 hours. After the reactor is cooled to room temperature the liquid content is analyzed by gas chromatography. Ten percent of the toluene is converted and the analysis of the products is shown in Table I. The selectivity of methyldiphenylmethane is 63 percent. The spent oxide can be regenerated by heating at 250° C.–600° C.

EXAMPLES 5–15

These examples are carried out under the same experimental conditions as Example 4 except that the catalysts indicated in Table I are used. The results are shown in Table I.

EXAMPLES 16–17

These examples are carried out under the same experimental conditions as Example 4, except that Example 16 uses $SnO_2$ as a support, and Example 17 uses $TiO_2$ as a support. The reactant-catalyst and results are given in Table I.

TABLE I

| Example | Reactant-Catalyst | 1 | 2 | 3 | 4 |
|---|---|---|---|---|---|
| 4 | $V_2O_5$ | 139.0 | 29.0 | 6.6 | 63 |
| 5 | $MoO_3$ | 11.0 | 3.8 | — | 81 |
| 6 | $Re_2O_7$ | 27.0 | 8.3 | 1.2 | 68 |
| 7 | $WO_3$ | 26.0 | — | — | 45 |
| 8* | $La_2O_3$ | 0.3 | — | — | 90 |
| 9 | $CuV_2O_6$ | 79.0 | 58.0 | 18.0 | 14 |
| 10 | $PbV_2O_6$ | 13.0 | 44.0 | — | 51 |
| 11 | $MgMoO_4$ | 3.0 | — | — | 99 |
| 12 | $CoMoO_4$ | — | 49.0 | — | 47 |
| 13 | $PbMoO_4$ | 4.0 | — | — | 95 |
| 14 | $La_2(MoO_4)_3$ | 1.0 | — | — | 99 |
| 15 | $H_3PMo_{12}O_{40}$ | 67.0 | 0.8 | 0.6 | 59 |
| 16 | $V_2O_5/SnO_2$ | 98.0 | 29.0 | 2.8 | 61 |
| 17 | $H_6V_{10}O_{25}/TiO_2$ | — | 8.6 | 3.7 | 72 |

*Not an example of the invention

In Table I, column 1 is the number of mg of toluene converted/g of catalyst; column 2 is percent of benzaldehyde; column 3 is the percent of benzoic acid; and column 4 is percent of methyldiphenylmethanes. As evidenced by the data shown in Table I, the oxides of vanadium, rhenium and molybdenum are most preferred catalysts because they give the highest combined conversions of reactants and selectivities toward the desired methyldiphenylmethanes.

EXAMPLE 18

A sample of 450 g of p-xylene is heated with 200 g of $V_2O_5$ in a one-liter autoclave at 260° C. for 4 hours. Nine percent of p-xylene is converted. The selectivity of (2,4',50-trimethyl)diphenyl methane is 73 percent.

I claim:

1. A process for preparing a (methyl-substituted)-diphenyl methane by a coupling reaction which process comprises contacting a methyl-substituted benzene with a solid heterogeneous catalyst having labile oxygen under conditions sufficient to form the (methyl-substituted)diphenyl methane, said catalyst being an oxygen-containing compound of vanadium, molybdenum, rhenium, tungsten or a combination of two or more thereof.

2. The process of claim 1 for preparing a (methyl-substituted)diphenyl methane by coupling a methyl-substituted benzene into the (methyl-substituted)diphenyl methane which comprises reacting the methyl-substituted benzene with a solid heterogeneous reactant-catalyst having labile oxygen under conditions whereby the (methyl-substituted)diphenyl methane is prepared, said catalyst being a compound of the formula $$M^1{}_aM^2{}_bM^3{}_cO_x \qquad \text{(III)}$$

wherein
M¹ is hydrogen;
M² is another element from Groups 1a–5a, 1b–7b and 8 of the Periodic Table of Elements as set forth in the *Handbook of Chemistry and Physics*, CRC, 48th Edition (1967–68);
M³ is at least one of V, Mo, Re or W;
a is 0 to 10;
b is 0 to 100;
c is 0.01 to 100; and
x is a number which satisfies the average valances of M¹, M² and M³ in the oxidation states in which they exists in reactant-catalyst.

3. The process of claim 2 wherein the catalyst is a solid heterogeneous reactant-catalyst selected from the group consisting of a vanadium oxide, a molybdenum oxide, a rhenium oxide and a bismuthmolybdate-containing catalyst.

4. The process of claim 2 wherein the temperature is from about 50° C. to about 700° C., and selectivity to carbon dioxide is at less than about 65 percent.

5. The process of claim 4 wherein the methyl-substituted benzene is toluene or xylene.

6. The process of claim 5 wherein the (methyl-substituted)diphenyl methane is prepared in a selectivity of at least 20 percent.

7. The process of claim 6 which is carried out in the vapor phase.

8. The process of claim 7 wherein the catalyst is molybdenum trioxide or vanadium pentoxide.

9. The process of claim 1 which is carried out in the liquid phase.

10. The process of claim 9 wherein the catalyst is molybdenum trioxide, vanadium pentoxide or rhenium heptoxide.

11. The process of claim 7 wherein an inert gaseous diluent is employed.

12. The process of claim 4 wherein the catalyst is a rhenium oxide or a tungsten oxide.

13. The process of claim 10 wherein the catalyst is deposited on an inert inorganic support.

14. The process of claim 1 wherein the catalyst is $H_3PMo_{12}O_{40}$ or vanadium pentoxide deposited on a stannous oxide support.

* * * * *